(12) United States Patent
Gray

(10) Patent No.: US 7,726,044 B2
(45) Date of Patent: Jun. 1, 2010

(54) CUSHIONING FOOT INSERT

(76) Inventor: Kevin Levin Gray, 535 E. Sanger St., Philadelphia, PA (US) 19120

( * ) Notice: Subject to any disclaimer, the term of this patent is extended or adjusted under 35 U.S.C. 154(b) by 1027 days.

(21) Appl. No.: 11/449,583

(22) Filed: Jun. 9, 2006

(65) Prior Publication Data

US 2007/0283598 A1    Dec. 13, 2007

(51) Int. Cl.
A43B 3/10    (2006.01)
A43B 19/00    (2006.01)
A43B 7/14    (2006.01)

(52) U.S. Cl. .................... 36/93; 36/96; 36/9 R; 36/71

(58) Field of Classification Search ............... 36/43, 36/44, 71, 9 R, 72 R, 8.3, 96, 93; D2/896, D2/980
See application file for complete search history.

(56) References Cited

U.S. PATENT DOCUMENTS

| | | | |
|---|---|---|---|
| 246,454 A | 8/1881 | Bruen | |
| 1,659,171 A | 2/1928 | Spafford | |
| 1,741,340 A | 12/1929 | Scholl | |
| 1,744,122 A | 1/1930 | Keeling | |
| 2,248,303 A | 7/1941 | Morgenroth et al. | |
| 2,266,317 A | 12/1941 | Hazen | |
| 2,288,199 A | 6/1942 | Levy | |
| 2,391,064 A | 12/1945 | McCandless | |
| 2,412,087 A | 12/1946 | Herbert | |
| 2,687,528 A | 8/1954 | Paul | |
| 2,771,691 A | 11/1956 | Luchs | |
| 2,776,500 A | 1/1957 | Gonsalves | |
| 2,810,214 A | 10/1957 | Wolfe | |
| 3,243,901 A | 4/1966 | Clarizio | |
| 3,334,356 A | 8/1967 | Abel | |
| 3,887,946 A | 6/1975 | Laskin et al. | |
| 4,249,319 A | 2/1981 | Yoshida | |
| 4,366,633 A | 1/1983 | Flottorp | |
| 4,658,515 A | 4/1987 | Oatman | |
| 4,862,605 A | 9/1989 | Gardner et al. | |
| 4,942,679 A | 7/1990 | Brandon et al. | |
| 5,123,180 A | 6/1992 | Nanning et al. | |
| 5,560,226 A | 10/1996 | Throneburg | |
| 5,791,163 A * | 8/1998 | Throneburg | ............... 66/178 R |
| 5,918,383 A | 7/1999 | Chee | |
| 5,935,671 A * | 8/1999 | Lhuillier | ............... 428/57 |
| 6,041,521 A | 3/2000 | Wong | |
| 6,044,497 A | 4/2000 | Richardson | |
| 6,282,816 B1 | 9/2001 | Rosendahl | |
| 6,367,087 B1 | 4/2002 | Spillman et al. | |
| 6,393,620 B2 | 5/2002 | Hatch et al. | |

(Continued)

*Primary Examiner*—Jila M Mohandesi
(74) *Attorney, Agent, or Firm*—Law Office of Peter G. Korytnyk, PLLC

(57) ABSTRACT

A foot insert is provided that is capable of providing protective cushioning to an area at the front of a wearer's foot including an area extending from the front tips of the toes to the metatarsal region of the ball portion of the foot. The foot insert includes a half-sock formed from a stretchable fabric material and is capable of extending over a toe portion up to about a mid-point of a length of a wearer's foot. A cushioning pad is attached to a lower sole portion of the half-sock and is formed from a shape-memory material that is capable of substantially permanently molding into a shape of a bottom portion and toes of the wearer's foot upon use.

19 Claims, 3 Drawing Sheets

U.S. PATENT DOCUMENTS

| | | |
|---|---|---|
| RE37,887 E | 10/2002 | Yates |
| 6,564,392 B1 | 5/2003 | Buckwald |
| D493,030 S | 7/2004 | Bartee |
| 6,810,603 B1 | 11/2004 | Cosentino |
| 7,051,457 B1 * | 5/2006 | Huggins et al. ............ 36/4 |
| 2005/0060911 A1 * | 3/2005 | Falone et al. ............ 36/44 |

* cited by examiner

CUSHIONING FOOT INSERT

FIELD OF THE INVENTION

The present teachings relate to a foot insert for reducing stress and pressure on a front part of a wearer's foot. In particular, the present teachings relate to a foot insert including a half-sock that slips over a front portion of the wearer's foot and having a cushioning pad made of shape-memory material secured to a lower sole portion thereof. The foot insert is adapted to cushion a wearer's foot in an area from the tips of the toes to the metatarsal region of a ball portion of the wearer's foot.

BACKGROUND OF THE INVENTION

A common problem experienced by athletes and non-athletes alike when wearing shoes is the shifting of weight toward the ball and toe portions of their feet and shoes. The toe and ball portions of a foot, and more particularly, a metatarsal region of the ball portion of the foot, generally receive a majority of the normal pressures of the foot when a person walks and/or runs during the course of the day. Moreover, experiencing such pressures intermittently when making sudden stops or cuts while participating in more vigorous activities such as football or soccer, for example, may also cause severe soreness, callouses, and/or foot damage known as 'turf toe'.

Furthermore, individuals already suffering from various frontal foot maladies such as, for example, calluses, corns, and hammertoes, are oftentimes unable to comfortably wear shoes and, therefore, resort to the use of one or more different types of known toe and/or foot pads to mitigate the pain. The daily or semi-daily use of these known toe and/or foot pads can provide limited results and can involve a relatively complex and time-consuming application procedure. As a result, some individuals resort to wearing larger shoes to reduce or eliminate the agitation of their foot maladies. However, oversized shoes can introduce new foot discomfort because they do not properly fit the foot.

Accordingly, a need exists for a device that can be readily slipped onto a front portion of a foot and that can cushion and protect the foot against pressures created by the shifting of weight toward the front of a shoe. In particular, a need exists for a device that is capable of readily conforming to the shape of the wearer's front foot and cushioning it from various pressures encountered during activities ranging from casual walking to strenuous sporting activities requiring sudden stops and/or lateral movement.

SUMMARY OF THE INVENTION

The present teachings disclose a foot insert and protector that is capable of providing protective cushioning to a frontal area of a wearer's foot.

According to the present teachings, the foot insert comprises a half-sock formed from a stretchable fabric material and includes an upper foot portion and a lower sole portion. The half-sock is capable of extending over a toe portion up to about a mid-point of a length of a wearer's foot when inserted into the foot insert. A cushioning pad is attached to the lower sole portion of the half-sock. The cushioning pad is formed from a shape-memory material that is capable of substantially permanently molding into a shape of a bottom portion of the wearer's foot upon use. The cushioning pad is adapted to extend from a front toe tip to a mid-area of the bottom portion of the wearer's foot during use such that cushioning is provided to substantially an entire ball portion, front toe tips, and toe bottoms of the wearer's foot.

The present teachings also describe a foot protector for a toe and ball portion of a wearer's foot. The foot protector includes a sock formed from a stretchable fabric material and shaped to conform to the front of the wearer's foot. The sock includes a closed end and extending sides arranged adjacent to an open end that is capable of being placed over the wearer's toes and up to a mid-point of a length of the foot. A cushioning pad is attached to the sock and formed from a shape-memory material. The cushioning pad is sized such that when a wearer's foot is inserted into the sock, the cushioning pad extends from a front tip portion of at least one of the toes to a metatarsal region of a ball portion at a bottom of the wearer's foot.

Additional features and advantages of various embodiments will be set forth, in part, in the description that follows, and, in part, will be apparent from the description, or may be learned by practice of various embodiments. The objectives and other advantages of various embodiments will be realized and attained by means of the elements and combinations particularly pointed out in the description herein.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Figure 1:
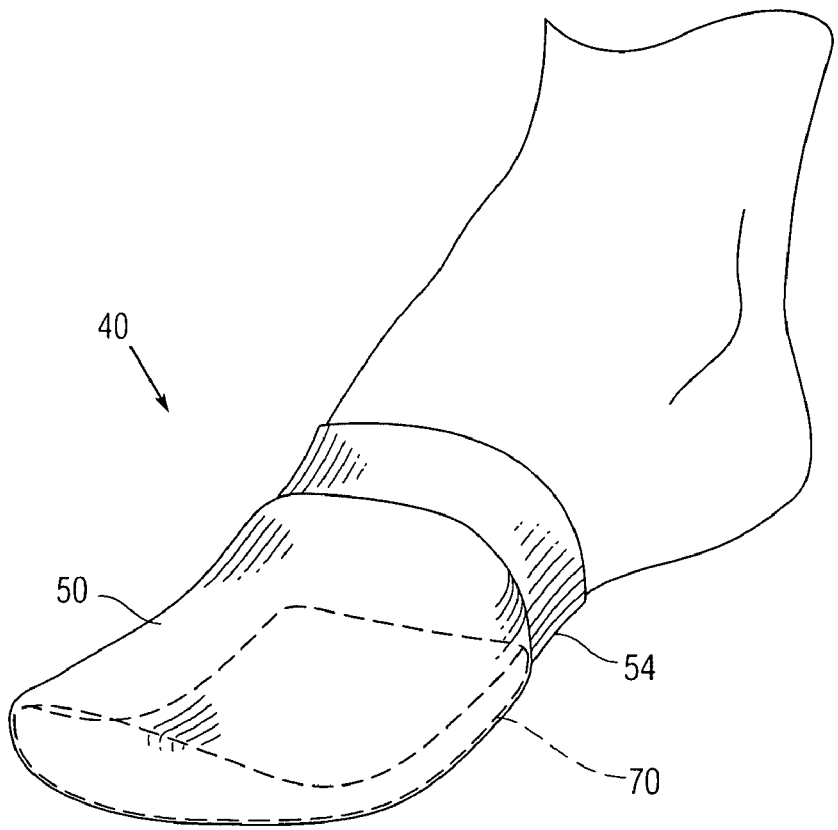
FIG. 1 is a perspective view of a front portion of a wearer's foot inserted into a foot insert according to the present teachings.

Referring to FIG. 1, the present teachings are directed to a foot insert or foot protector 40 that can be worn directly on the front portion of a foot or over any hosiery (not shown) already placed on the foot. The foot insert 40 is preferably designed and constructed to provide protective cushioning by molding specifically to an area at the front of a wearer's foot. This area extends from the front tips of the toes to the metatarsal region of the ball portion of the foot, located approximately at a mid-point of a length of a wearer's foot. This area includes the bottom or planar surface of the ball portion and toes of the wearer's foot, as well as peripheral areas including the tips of one or more of the toes.

When walking, running, competing athletically, and the like, it has been found that the toes and ball portion, and more particularly, a metatarsal region of the ball portion of the foot, receive a majority of the pressures and forces experienced by the foot. For example, wearing athletic shoes while participating in activities requiring sudden stops or cuts for extensive periods of time may cause pain, soreness, callouses, bunions, hammer toes, plantar pressure, and other possible foot damage such as 'turf toe' to the wearer. The foot insert 40 according to the present teachings addresses at least these problems by providing cushioning to a relatively large frontal area of the foot, including the area surrounding the toes and ball portion of the wearer's foot, thereby concentrating cushioning where needed most. It is contemplated that the foot insert or foot protector 40 of the present teachings can be advantageously used with various types of shoes or foot coverings, such as, for example, work shoes, boots, designer footwear, sneakers or tennis shoes, and the like, and will help reduce plantar pressure and generally provide the wearer with increased comfort when walking, climbing, running, cycling, and during various other activities.

Figure 2:
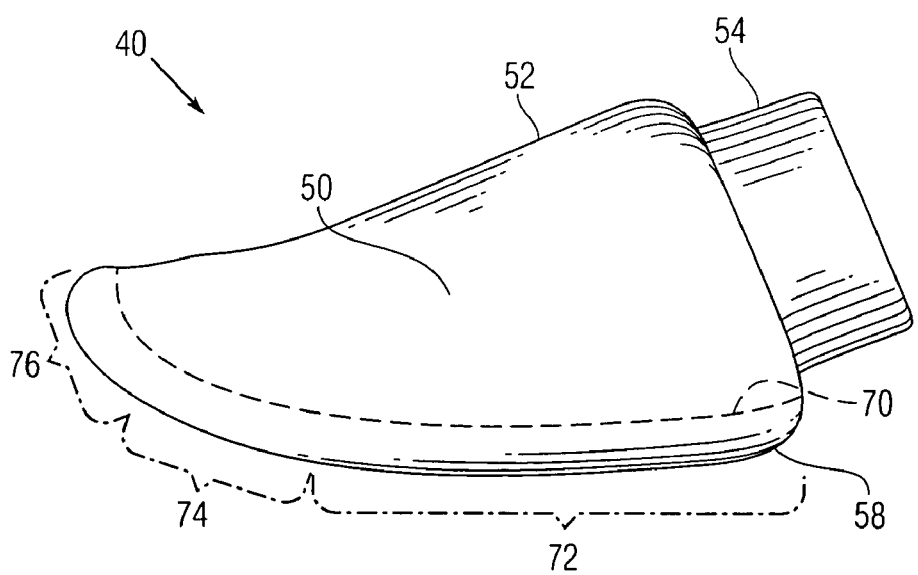
FIG. 2 is a side view of the foot insert according to the present teachings without a wearer's foot inserted therein.
Figure 3:
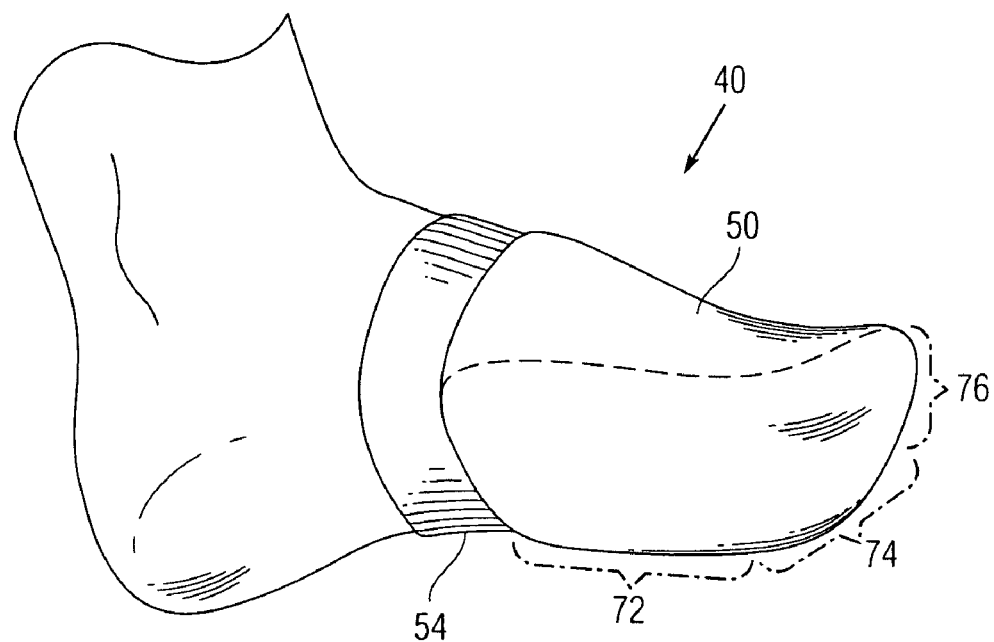
FIG. 3 is a perspective view of a bottom front portion of a wearer's foot inserted into the foot insert according to the present teachings.

As shown in FIGS. 1-3, the foot insert 40 preferably includes a half-sock 50, formed from a stretchable fabric material, and a cushioning pad 70 secured to the half-sock 50. The cushioning pad 70 is sized to provide cushioning to an area surrounding the toes 74, 76 to a ball portion 72 at the bottom of a wearer's foot. The cushioning pad 70 is preferably formed of a shape-memory material, such as, for example, memory foam or a gel, and is arranged to contact and underlie the ball portion 72, as well as the areas of the toes of the wearer's foot, including the bottom 74 and tips 76 of the toes, as shown in FIGS. 2 and 3. The shape-memory gel of the cushioning pad 70 can be a silicon gel. It will also be understood by those skilled in the art that the cushioning pad 70 can be secured to the half-sock 50 by an adhesive and/or by other types of securement mechanisms, such as stitches or rivets, for example.

The shape-memory material of the cushioning pad 70 and the general design of the foot insert 50 allows it to readily mold to a wearer's foot and shoe, and permanently keep the molded shape. Accordingly, if the foot insert 50 is worn on the opposite foot or in a different type of foot apparel, it will not properly fit or provide a required level of comfort.

The half-sock 50 is preferably formed of a fibrous material, such as, for example, nylon, wool, cotton, or any other fibrous material that can help reduce perspiration and odors. The fibrous material can be stretchable such that the foot insert 40 can conform to a wide range of wearer's feet. As best illustrated in FIGS. 2 and 3, the foot insert 40 can also preferably include an elastomeric portion 54 which at one end forms the open end where the wearer's foot is inserted. The elastomeric portion 54 is arranged to securely position the open end of the foot insert 40 about the metatarsals or up to about the beginning of the arch of a typical wearer's foot. The half-sock 50 can be designed to incorporate dual layers of material. For example, the cushioning pad 70 can be secured to the half-sock 50 and then sealed between the dual layers of material so as not to allow the cushion pad 70 to be movable therein. As shown in FIG. 2, the foot insert 40 has a specific top and bottom whereby the cushioning pad 70 is secured to a lower sole portion 58 of the half-sock 50, and the top of the half-sock 50 encompasses an upper foot portion 52.

Figure 4:
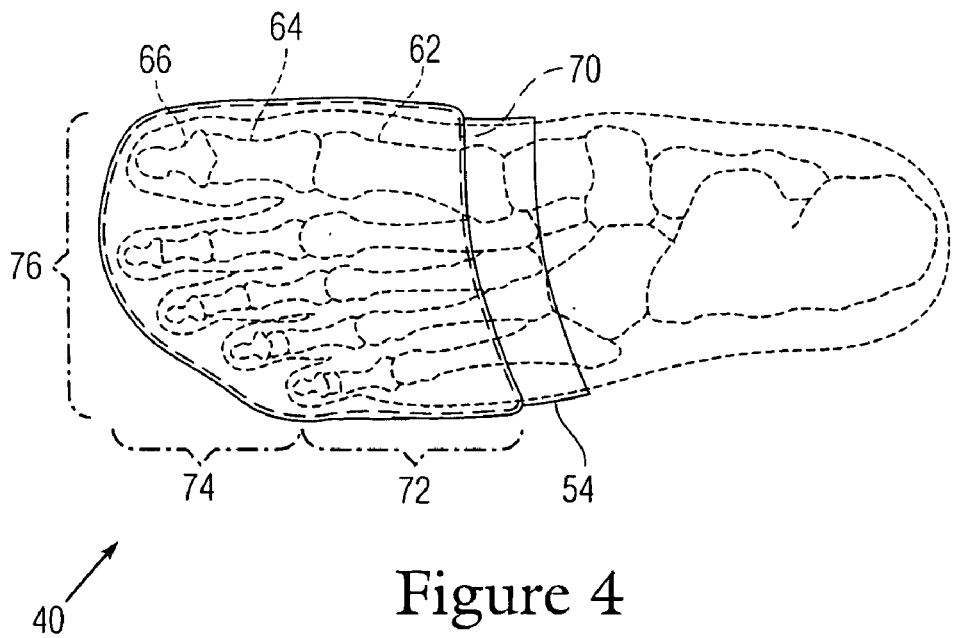
FIG. 4 is a bottom plan view of the foot insert according to the present teachings being worn on a wearer's foot, the bones of the wearer's foot being shown in phantom.

FIG. 4 illustrates a bottom plan view of the foot insert 40 of the present teachings positioned on a foot of a wearer. As understood by those skilled in the art, the bones of the wearer's foot are shown in phantom. The bones of the foot that are cushioned and protected by the foot insert 40 of the present teachings include the metatarsals 62, the phalanges 64, and the toe bones 66. As shown in FIG. 4, the cushioning pad 70 of the foot insert 40 of the present teachings is arranged to protect the metatarsal region of the ball portion 72 of the wearer's foot, up to and including the bottoms 74 and frontal tips 76 of the toes, thereby concentrating cushioning where needed most. As understood by those skilled in the art, the base of the phalanges 64 according to the present teachings preferably form a portion of the ball portion 72, but may also be considered to include peripheral edges of the toe portion 74 of a wearer's foot.

Figure 5:
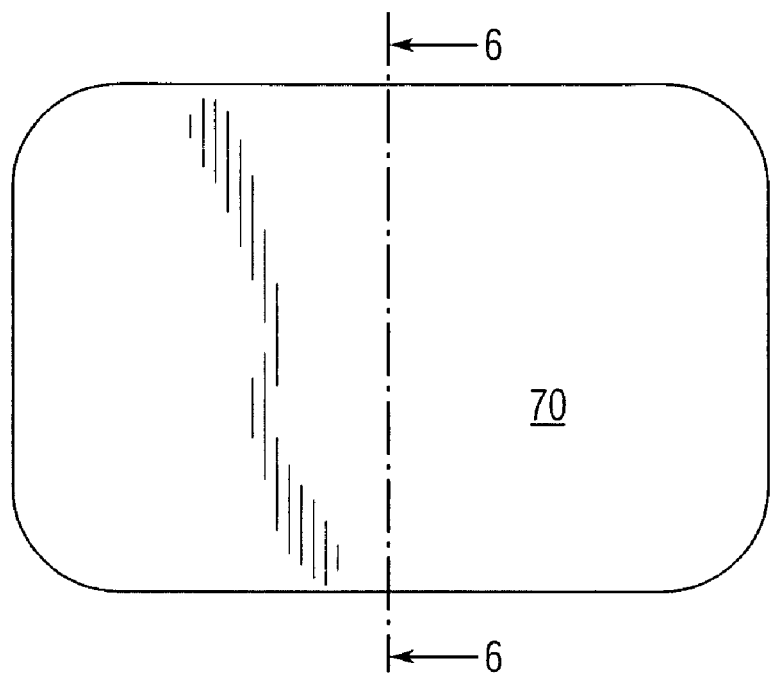
FIG. 5 is a top view of a cushioning pad of the foot insert according to the present teachings.
Figure 6:
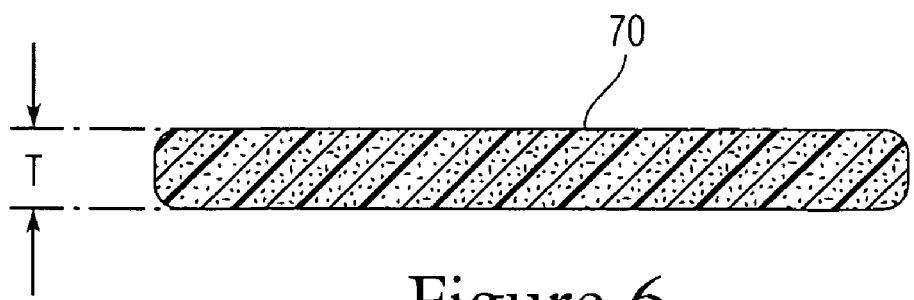
FIG. 6 is a cross-sectional side view of the cushioning pad taken along line 6-6 of FIG. 5.

The cushioning pad 70 can extend across the entire width of the wearer's foot and can have a generally rectangular shape when not attached to the half-sock 50 in a relaxed state, as shown in FIG. 5. When secured within the half-sock 50, the cushioning pad 70 can be arranged to curl upwardly at the tips 76 of the toes, see FIGS. 2 and 3. In use, the shape of the cushioning pad 70 allows one end thereof to curl about one or more of the tips of the wearer's toes and provide cushioning in a direction that is generally parallel to the wearer's foot. Referring to FIG. 6, the cushioning pad 70 can have a thickness, T. The thickness, T, can vary depending on the amount of cushioning to be provided. For example, the thickness can preferably be from about ¼ inch to about 1 inch, or larger. However, the dimensions of the cushioning pad 70 may vary with various factors, such as, for example, the desired size range of potential users of the foot insert 40.

The foot insert 40 of the present teachings provides superior cushioning and protection when used with athletic shoes, but also provides benefits when used by the casual, formal, and work apparel shoe wearer, including people with certain medical conditions. The foot insert 40 is designed to reduce plantar pressure and can provide increased comfort during walking or running. For athletes, the foot insert 40 helps increase comfort to the plantar and toe areas of the foot and helps to prevent or reduce the severity of 'turf toe' which often effects athletes who make sudden stops or cuts while running.

For everyday use, the foot insert 40 of the present teachings allows individuals to be more comfortable in a work shoe, boot, designer footwear, and the like, especially when walking, climbing, or running. With respect to medical applications, the foot insert 40 will allow people with narrow feet to fill out their foot apparel by filling-in extra space in their shoes. This allows the shoe to have a snugger fit on the foot and helps prevent or reduce slippage, thereby eliminating blistering, and the like. Moreover, the foot insert 40 allows wearers to fit into a bigger size shoe when they are experiencing one or more foot issues, such as calluses, corns, hammertoes, or other foot maladies. This allows wearers to walk comfortably and as normal as possible when wearing shoes larger than their true size. Moreover, the foot insert 40 of the present teachings can provide better foot cushioning for people with diabetes.

The foot insert 40 of the present teachings also provides aesthetic advantages. The foot insert 40 allows the top portion of foot apparel to look more attractive longer by helping to minimize the formation of creases that occur in a shoe over time. This is achieved because the foot insert 40 operates like a shoe tree by keeping the shape of the shoe intact by filling in loose spaces which causes the creasing.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A foot insert comprising:
a half-sock formed from a stretchable fabric material and including an upper foot portion and a lower sole portion, the half-sock being capable of extending over a toe portion up to about a mid-point of a length of a wearer's foot when inserted into the foot insert; and a memory gel pad attached to the lower sole portion of the half-sock, the memory gel pad being formed from a shape-memory material that is capable of substantially permanently molding into a shape of a bottom portion of the wearer's foot upon use, the memory gel pad being adapted to curl about at least one front toe tip during use and extend to a mid-area of the bottom portion of the wearer's foot while extending across a width of the bottom of the wearer's foot through each metatarsal such that cushioning is provided to substantially an entire ball portion, front toe tips, and toe bottoms of the wearer's foot.

2. The foot insert of claim 1, wherein the memory gel pad is adapted to extend substantially entirely across a width of the bottom of the wearer's foot at a location where at least a half of a length of each metatarsal is cushioned by the memory gel pad when the wearer's foot is inserted into the foot insert.

3. The foot insert of claim 1, wherein the shape-memory material of the memory gel pad includes a memory foam.

4. The foot insert of claim 3, wherein the gel is a silicon gel.

5. The foot insert of claim 1, wherein the stretchable fabric material of the half-sock is one of nylon, wool, and cotton, or a combination thereof.

6. The foot insert of claim 1, wherein the half-sock includes a double wall including in inner fabric material layer and an outer fabric material layer.

7. The foot insert of claim 6, wherein the memory gel pad is arranged between the inner fabric material layer and the outer fabric material layer.

8. The foot insert of claim 1, wherein the memory gel pad has a thickness of at least about ¼ inch.

9. The foot insert of claim 1, wherein the memory gel pad is generally rectangular in shape.

10. A foot protector for a toe and ball portion of a wearer's foot comprising:

a sock formed from a stretchable fabric material and shaped to conform to the front of the wearer's foot, the sock including a closed end and extending sides arranged adjacent to an open end that is capable of being placed over the wearer's toes up to a mid-point of a length of the foot; and a memory gel pad formed from a shape-memory material and being attached to the sock, the memory gel pad being sized such that when a wearer's foot is inserted into the sock the memory gel pad curls about a frontal tip portion of at least one of the toes and extends to a metatarsal region of a ball portion at a bottom of the wearer's foot and across a width of the ball portion through each metatarsal.

11. The foot protector of claim 10, wherein the memory gel pad is sized to curl about a frontal tip portion of at least three of the toes of the wearer's foot during use.

12. The foot protector of claim 10, wherein the memory gel pad is sized to extend substantially entirely across a width of the ball portion of the wearer's foot at a location where at least a half of a length of each metatarsal is cushioned by the memory gel pad during use.

13. The foot protector of claim 10, wherein the shape-memory material of the memory gel pad includes a memory foam.

14. The foot protector of claim 13, wherein the gel is a silicon gel.

15. The foot protector of claim 10, wherein the stretchable fabric material of the half-sock is one of nylon, wool, and cotton, or a combination thereof.

16. The foot protector of claim 10, wherein the sock includes a double wall including in inner fabric material layer and an outer fabric material layer.

17. The foot protector of claim 16, wherein the memory gel pad is arranged between the inner fabric material layer and the outer fabric material layer.

18. The foot protector of claim 10, wherein the memory gel pad has a thickness of at least about ¼ inch.

19. The foot protector of claim 10, wherein the memory gel pad is generally rectangular in shape.

* * * * *